United States Patent [19]

French et al.

[11] Patent Number: 5,545,374
[45] Date of Patent: Aug. 13, 1996

[54] MICROBICIDAL COMPOSITIONS

[75] Inventors: Madeline S. French, Runcorn; Anita J. Harvey, Warrington, both of United Kingdom

[73] Assignee: Solvay Interox Limited, Warrington, England

[21] Appl. No.: 464,743

[22] PCT Filed: Dec. 9, 1993

[86] PCT No.: PCT/GB93/02520

§ 371 Date: Jun. 21, 1995

§ 102(e) Date: Jun. 21, 1995

[87] PCT Pub. No.: WO94/14321

PCT Pub. Date: Jul. 7, 1994

[30] Foreign Application Priority Data

Dec. 24, 1992 [GB] United Kingdom .................. 9227020

[51] Int. Cl.$^6$ .................. A61L 2/18; A01N 37/16
[52] U.S. Cl. .................. 422/28; 510/218; 510/234; 510/372; 514/557; 252/186.42

[58] Field of Search .................. 422/28; 252/94, 252/95, 96, 97, 98, 99, 100, 101, 102, 103, 104, 106

[56] References Cited

U.S. PATENT DOCUMENTS 4,783,278 11/1988 Sanderson et al. .................. 252/95

FOREIGN PATENT DOCUMENTS 0397217 11/1990 European Pat. Off. .

Primary Examiner—Robert J. Warden
Assistant Examiner—Theresa T. Snider
Attorney, Agent, or Firm—Larson and Taylor

[57] ABSTRACT

Microbicidal compositions having activity over a broad pH range are provided. The compositions include a peracid and a nonionic surfactant according to the general chemical formula: $R\text{-}(OCH_2CH_2)_n\text{-}(OCH_2CH_2CH_3)_p\text{-}OH$, wherein R represents an alkyl group of at least 6 carbon atoms, and n and p each represent an integer. The compositions can additionally include a cationic surfactant.

17 Claims, No Drawings

MICROBICIDAL COMPOSITIONS

BACKGROUND OF THE INVENTION

The present invention concerns microbicidal compositions. More specifically, the present invention concerns peracid microbicidal compositions, and still more specifically, peracid microbicidal peracid compositions having activity over a broad pH range.

The use of aliphatic peracids as microbicides is well known in the art. Such solutions have found favor because they offer a microbicidal system which has reduced environmental impact and are completely biodegradable. For example, European patent application 0 193 41 6 discloses peracetic acid compositions comprising simple, non-capped alcohol ethoxylates. It has also long been recognized that the microbicidal activity of aliphatic peracids is strongly dependant on the pH at which the peracid is employed, and that the activity decreases as the pH increases. This is particularly evident as the pH of the peracid solution approaches neutral pH. Accordingly, the most effective use of aliphatic peracid microbicides has hitherto occurred at acidic pH. A number of systems require disinfection at alkaline pH or exist in their natural state at alkaline pH, and are thus not well suited to disinfection by such peracid-based microbicides. It remains an ongoing desideratum to identify peracid-based microbicide compositions having activity over a broader and/or higher pH range.

It is an object of certain aspects of the present invention to provide aliphatic peracid microbicide compositions having improved activity over a broader and/or higher pH range.

It is a further object of some or other aspects of the present invention to provide microbicidal compositions having improved activity against gram negative bacteria over a broader and/or higher pH range.

BRIEF SUMMARY OF THE INVENTION

According to the present invention, there are provided peracid compositions having microbicidal activity over a broad pH range, characterized in that they comprise an effective amount of a peracid and an ethoxylated and propoxylated alcohol nonionic surfactant according to the general chemical formula (1):

$$R\text{-}(OCH_2CH_2)_n\text{-}(OCH_2CHCH_3)_p\text{-}O\text{-}H$$

wherein R represents an alkyl group of at least 6 carbon atoms n and p each represent an integer.

According to a second aspect of the present invention, there is provided a microbicidal process employing as microbicide an effective amount of a peracid and an ethoxylated and propoxylated alcohol nonionic surfactant, characterised in that the nonionic surfactant has the general formula:

$$R\text{-}(OCH_2CH_2)_n\text{-}(OCH_2CHCH_3)_p\text{-}O\text{-}H$$

wherein R represents an alkyl group of at least 6 carbon atoms n and p each represent an integer.

DESCRIPTION OF PREFERRED EMBODIMENTS

By employing the selected nonionic alkoxylated alcohol surfactant of formula (1), it has been found that the effectiveness of peracid microbicides is enhanced at treatment pHs of above pH 6, i.e. in approximately neutral or mildly alkaline pH conditions, thereby extending advantageously the effective treatment range for the peracids.

In formula (1), R often contains from about 6 to about 18 carbons, and especially from about 8 to about 12 carbons and in many instances comprises a linear group. R can be synthetically derived, or can be obtained from natural sources, for example, from tallow. The weight proportion of alkoxylate i.e. ethoxylate or the total of ethoxylate and propoxylate in the surfactant is often selected in the region of about 55% to about 90%; n+p in formula (1) in many instances totalling from 4 to 20.

It will be recognized that compositions according to the present invention can be supplied in a number of different forms or can be produced immediately prior to use depending, for example, on the particular composition desired, or on the particular application. For instance, in certain embodiments of the present invention, the composition is in the form of a ready-to-use solution which can be used without requiring dilution. In certain other embodiments, the composition is in the form of a concentrated solution which may be employed without dilution, but is primarily intended for dilution prior to use. In further embodiments, the components are provided as a two pack system, with the first solution comprising aqueous peracid solution and optionally a fraction of the nonionic surfactant, and the second solution comprising the remaining fraction of the nonionic surfactant. In these two pack systems, the second solution can be used to dilute the first solution to produce a composition ready for immediate use, or a composition which can be diluted further prior to use.

The weight of alkoxylated alcohol in the invention compositions can be selected within a wide range. In many embodiments, where the compositions are ready for use or supplied as a concentrate, it is at least 0.1% w/w and often is not greater than about 50% w/w. Advantageous results have been obtained for ready to use solutions at a concentration chosen in the range of about 4 to about 15% w/w of the alkoxylated alcohol. Where a concentrate is diluted prior to use, the concentration of alcohol ethoxylate in the diluted solution is often in the range of from about 0.1% w/w to about 15%w/w.

Where the components are provided as a two pack system, the second solution can contain up to 100% of nonionic surfactant, however, in many embodiments, the nonionic surfactant will be present at from about 20% w/w to about 80% w/w. When nonionic surfactant is employed in the first solution in a two pack system, the concentration of the nonionic surfactant is typically in the range of from about 4 to about 25% w/w.

The peracid can comprise any percarboxylic acid, particularly water-soluble percarboxylic acids and especially is selected from low or medium molecular weight aliphatic percarboxylic acids such as those containing up to 9 carbons. The invention will be described with particular reference to peracetic acid, but for example, perpropionic acid may be employed instead of or together with peracetic acid.

The concentration of peracid in preformed compositions intended for storage and/or transportation can be selected over a wide range, such as from about 0.01% to 40% w/w. In many embodiments, the compositions comprise a dilute solution of the peracid, such as from about 0.5% to about 10% w/w. The actual selection of the peracid is often a matter at the discretion of the producer, for his own convenience, balancing the beneficial and disadvantageous effects of a chosen concentration. Concentrations of around 2 to 3% w/w peracid and from about 4 to about 5.5% w/w peracid are quite popular as compromises that are readily transportable without transporting too much water. The weight ratio of nonionic surfactant to peracid is often selected to be in the range of from 10:1 to 1:5, and preferably from 4:1 to 1:1.

In many desirable compositions according to the present invention, which are intended for storage and or transportation, the peracid is made by a reaction between the corresponding carboxylic acid or carboxylic acid anhydride and hydrogen peroxide in an aqueous medium. It is particularly desirable to employ compositions in which the peracid is present at a concentration that is substantially in equilibrium with residual concentrations of its corresponding carboxylic acid and hydrogen peroxide. In such compositions, the concentration of hydrogen peroxide is often selected in the range of from about 0.1 to 30% w/w and the concentration of carboxylic acid from about 0.5 to about 50% w/w. In practice, the weight ratio of carboxylic acid e.g. acetic acid or hydrogen peroxide relative to the peracid can be varied at the discretion of the producer/user within the entire range, provided that an appropriate concentration of the other reagent is present. In general terms, for a stable equilibrium, a low peroxide concentration is balanced by a high carboxylic acid concentration, and vice versa, and ratio of peroxide plus carboxylic acid to peracid increases as the concentration of peracid decreases. For many dilute, transportable peracid compositions containing less than 6% peracid, and often greater than 1% peracid, the weight ratio of peroxide to peracid and of carboxylic acid to peracid are each often selected in the range of from about 1:10 to about 10:1.

The transportable compositions can be employed neat, for example in the disinfection of hard surfaces such as work surfaces, equipment or sanitary ware, particularly if they contain less than 6% peracid, but they are often diluted with water before use or it is an aqueous medium which it is intended to disinfect. The extent of dilution is at the discretion of the user, taking into account the extent and nature of the infecting micro-organisms which it is desired to kill, the period available for the kill and the operational conditions such as the temperature. Where the disinfection process involves a manual treatment stage, for example, distributing a composition over a hard surface with a cloth, it is often desirable that the peracid concentration in the solution in use is less than about 0. 1%.

It is convenient to express the concentration of the disinfectant composition by reference to the concentration of the peracid. The alkoxylated alcohol is present at a relative concentration thereto as indicated previously herein. The peracid concentration is usually at least 5 mg/l and often up to 1000 mg/l. For a number of micro-organisms, a concentration of between 25 and 400 mg/l is selected. Depending on the conditions, though, for shock treatments, peracid concentration of above 1000 mg/l, for example up to about 10000 mg/l can be contemplated and for prolonged contact, a concentration of 1 to 5 mg/l peracid can sometimes be appropriate.

It will be recognized that the advantage of the invention composition, compared with prior disclosed compositions not containing the alkoxylated alcohol, is that it is relatively more effective at approximately neutral or mildly alkaline compositions, and especially at a pH of from above 6 to 8. The user can obtain the benefit of a similar extent of disinfection using a peracid composition, such as peracetic acid at a higher pH, i.e. avoiding or reducing the extent of pH adjustment, or alternatively he can obtain improved disinfection if he chooses not to acidify.

In theory, microbicidal compositions can contain other active microbicides in order to augment the activity from peracids, but there can be no guarantee that the addition of further components will improve the ova;rail microbicidal effectiveness. Some combinations of peracid with other components are unstable and others show little or no detectable change in performance, at least with reference to various widespread target micro-organisms.

One such class of other microbiocides comprises quaternary ammonium compounds, a class of carbonic surfactants. They are widely available, and hence are attractive, but there can be difficulties associated with their use. Within the spectrum of micro-organisms that it is desired to control, i.e. kill or inactivate, by the application of a microbicidal composition are bacteria. Bacteria themselves are generally divided into two classes, gram-negative and gram-positive bacteria. It is generally recognized that, of the two classes, gram-positive bacteria are, in many cases, relatively easy to control by the application of quaternary ammonium compounds, but that gram negative bacteria are much more resistant to them. It is particularly desirable to control gram negative bacteria, because the group comprises many well known pathogens, for example, many species of faecal bacteria, pseudomonads which can cause skin irritation, and other species of bacteria, such as salmonella which can cause food poisoning. Self-evidently, it would be advantageous to identify microbicidal compositions having improved activity against gram negative bacteria.

It has been found to be especially desirable to employ the combination of peracid and alkoxylated alcohol in conjunction with a quaternary ammonium cationic surfactant, since by so doing, the resultant three component combination has been shown to be particularly effective against gram negative bacteria. The quaternary ammonium compound, which can be represented by the general formula $R^aR^bR^cR^dN+Q^-$ in which substituents $R^a$, $R^b$, $R^c$, and $R^d$ each represent an alkyl or aryl group or two of which combine with the nitrogen to form a heterocyclic nucleus, the total number of carbons in $R^a$ to $R^d$ normally comprising from about 10 to about 30 carbons. One or two of the substituents normally contains from 8 to 18 linear carbons often from C12 to C16, or forms part of the heterocyclic nucleus such pyridinium. One of the substituents can conveniently comprise a benzyl group. The remaining substituents usually are selected from C1 to C4 alkyl groups, and especially methyl or ethyl. Q represents a counterion such as hydroxyl, sulphate or alkyl sulphate.

The quaternary ammonium cationic surfactant (QACS) is often incorporated at a relatively small proportion of the overall composition, such as up to about 5% w/w in a dilutable composition, or up to about 0.5% w/w in a composition ready for use without further dilution. It will be recognised that in a two pack system, the QACS can be incorporated in either or both of the solutions at a concentration selected accordingly.

A particularly effective range of compositions comprises peracetic acid at a weight concentration in the region of about 2.0 to 5.5%, preferably in the presence of sufficient hydrogen peroxide and acetic acid selected together in the ranges of 1 to 20% and 1 to 50% respectively to obtain an equilibrium composition, from 4 to 15% alkoxylated alcohol and from 0.05 to 0.5% QACS. Such compositions may often be diluted by a factor in the range of from about 10 to about 1000, depending on the peracid concentration before dilution and its desired concentration for disinfection.

The invention compositions are particularly intended for use in the food, beverage and allied industries. The beverage industries include brewing, wine-making and alcohol distillation, and in dairies. In such industries, it is especially important to guard against the contamination of food and drink intended not only for human consumption, but also that intended for consumption by livestock, and pets. In such industries, the compositions can be used to disinfect brewing vessels, or surfaces that come into contact with prepared food or drink which in normal circumstances would be consumed without cooking. Those surfaces can include food mixing or washing vessels, transport equipment such as conveyors, arid filling and packaging equipment. Compositions for use in these industries generally contain or are diluted in uses to peracid concentrations of below 500 mg/l with corresponding concentrations of the other constituents. Such diluted compositions in practice are rarely non-equilibrium in that over a period of time there would be a tendency for the peracid to re-equilibrate to hydrogen peroxide and carboxylic acid, but that is acceptable under disinfection treatment times The use of the two component composition enables the process to be effected often without any pH alteration, and the use of the three component composition is especially desirable in that it combines the advantage of the two component combination with that of a wider spectrum activity, even at approximately neutral or alkaline pH.

The compositions according to the present invention can be prepared by mixing a first solution comprising a peracid, with a second solution comprising an ethoxylated and propoxylated alcohol nonionic surfactant according to the general chemical formula (1):

$$R-(OCH_2CH_2)_n-(OCH_2CHCH_3)_p-O-H$$

wherein R represents an alkyl group of at least 6 carbon atoms n and p each represent an integer.

Having described the invention in general terms, specific embodiments thereof will be described hereinafter in greater detail by way of non-limiting example only.

Comparisons CA to CD and Examples 1 and 2

In Comparison CA, the treatment employed was a dilutable grade of peracetic acid commercially available from Solvay Interox Limited under the Trade Mark PROXITANE, containing 5% peracetic acid, 10% w/w acetic acid and 20% w/w hydrogen peroxide, diluted to give an in use concentration of peracid of 50 mg/l for the bacteria, and 200 mg/l for the yeast.

In Comparison CB, the treatment employed comprised 0.2% w/v active ingredient of a quaternary ammonium cationic surfactant (QACS) available from Albright and Wilson under their Trade Mark EMPIGEN grade CM.

In Comparison CC, the composition employed comprised a solution of 10% w/v of an ethoxylated/propoxylated linear primary alcohol (alkoxylated alcohol) available from Union Carbide under their Trade Mark TRITON grade DF16.

In Comparison CD, the treatment employed was as in Comparison CA, except that 0.2% w/v active ingredient of the QACS of Comparison CB was also employed.

in Example 1, the treatment employed was as for Comparison CA, except that 10% w/v of the (alkoxylated alcohol) of Comparison CC was also employed.

In Example 2, the treatment employed was as for Example 1, except that 0.2% w/v active ingredient of the QACS of Comparison CB was also employed.

The effectiveness of each of the various Comparison and Example compositions as a microbicide was determined against three microbes considered to be representative for beverage industries, namely a yeast, *Candida albicans*, a gram negative bacterium, *Pseudomonas aeruginosa*, and a Gram-positive bacterium, *Staphylococcus aureus*.

The effectiveness of the composition as a microbicide was tested in a disinfectant suspension test. The microbicide was challenged with an inoculum of the microbe containing a measured concentration of between $1 \times 10^8$ to $3 \times 10^8$ cfu for bacteria and between $1 \times 10^7$ and $3 \times 10^7$ cfu for the yeast in the presence of yeast extract (0.4%) and standard hard water for a period of 5 minutes at ambient temperature. The composition was quenched in the standard manners for peracid and surfactants depending on which components are present and thereafter determining the number of viable micro-organisms by conventional plate culture techniques. The studies were conducted in duplicate.

The number of surviving viable bacteria or yeasts per unit volume (cfu) was then compared with the number before the disinfection treatment began, and the result given is the fraction that had been killed, expressed a logarithm, base 10; the higher the resultant number, the more effective the disinfection. The maximum for the yeast was 4.6, for the gram -ve bacterium was 6.3 and 5.9 for the Gram +ve bacterium.

The results of the disinfection studies are summarized in Table 1 below

TABLE 1

| | | Measured Log Reduction Factor for | | |
| --- | --- | --- | --- | --- |
| Trial | pH | Yeast | Gram −ve Bacteria | Gram +ve Bacteria |
| CA | 4 | 4.5 | 6.3 | 5.9 |
| | 6 | 3.3 | 3.5 | 4.4 |
| | 8 | 1.8 | 2.3 | 1.7 |
| | 10 | 0.3 | 1.4 | 0.6 |
| CB | 4 | 0.4 | 3.8 | 5.9 |
| | 6 | 0.7 | 0 | 5.9 |
| | 8 | 3.4 | 0 | 5.9 |
| | 10 | 4.6 | 0 | 5.9 |
| CC | 4 | 0.5 | 1.9 | 1.8 |
| | 6 | 0.7 | 0 | 0.7 |
| | 8 | 0.6 | 0 | 0.9 |
| | 10 | 0.6 | 0 | 1.1 |
| CD | 4 | 4.6 | 6.3 | 5.9 |
| | 6 | 4.6 | 3.5 | 5.9 |
| | 8 | 4.6 | 2.3 | 5.9 |
| | 10 | 4.6 | 1.1 | 5.9 |
| Ex 1 | 4 | 4.6 | 6.3 | 5.9 |
| | 6 | 4.1 | 6.3 | 5.9 |
| | 8 | 2.9 | 4.9 | 5.0 |
| | 10 | 0.6 | 1.9 | 1.9 |
| Ex 2 | 4 | 3.1 | 6.3 | 5.9 |
| | 6 | 0.6 | 6.3 | 5.9 |
| | 8 | 4.6 | 6.3 | 5.9 |
| | 10 | 4.5 | 2.5 | 4.5 |

From Table 1, it can be seen in Comparison CA that the effectiveness of peracetic acid as a microbicide is very good at acidic pHs of the region of pH 4, but that its effectiveness diminishes as the pH of the solution containing the yeast or bacterium increases. A comparison of Comparisons CA with CB and CD shows that the QACS complements the peracetic acid in terms as the pH varies through the range tested for the yeast, without demonstrating synergism, but that there is no complementary action for the bacteria. A comparison of Comparisons CA, CC and Example 1 demonstrates that the combination of the alkoxylated alcohol and peracetic acid offers similar performance to that of peracetic acid alone, at the low pH, and at higher pHs of from pH 6 to pH 10 shows synergism especially for the Gram negative bacteria which are resistant to QACS. Thus, Table 1 shows that the pH range in which peracids retain their effectiveness is visibly extended from about pH 4 without the alkoxylated alcohol up as high as about pH 8 with the alkoxylated alcohol. Table 1 also shows complementary results or synergistic results for the Gram positive bacteria and the yeast at the higher pHs.

From a comparison of Examples 1 and 2, it can be seen that the addition of the QACS is beneficial at the high end of the pH range, and particularly at about pH 8, complementing the other components and producing a composition that is especially effective for all three of the test microorganisms.

Storage Stability Trial

To 247.5 g of a sample of peracetic acid commercially available from Solvay Interox Limited under the Trade Mark PROXITANE, containing 5% peracetic acid, 10% w/w acetic acid and 20% W/w hydrogen peroxide was added 0.11 g of a quaternary ammonium cationic surfactant (QACS) available from Albright and Wilson under their Trade Mark EMPIGEN grade CM and 2.39 g of an ethoxylated/propoxylated linear primary alcohol (alkoxylated alcohol) available from Union Carbide under their Trade Mark TRITON grade DF16. After 160 days storage at ambient temperature (ca. 20°–25° C.), analysis of the sample showed that 95% of the peracetic acid was retained, indicating that the sample had excellent storage stability.

We claim:

1. An acidic, storage stable peracid disinfectant solution comprising an aqueous solution comprising an amount effective for disinfection of an aliphatic peracid containing up to 9 carbon atoms and an ethoxylated and propoxylated alcohol nonionic surfactant according to the general formula:

$$R\text{-}(OCH_2CH_2)_n\text{-}(OCH_2CHCH_3)_p\text{-}OH$$

wherein R represents an alkyl group of at least 6 carbon atoms and n and p each represent an integer.

2. A solution according to claim 1, wherein the nonionic surfactant and peracid are present in a weight ratio within the range of from 10:1 to 1:5.

3. A solution according to claim 2, wherein the nonionic surfactant and peracid are present in a weight ratio within the range of from 4:1 to 1:1.

4. A solution according to any one of claims 1, 2, or 3, wherein the solution contains from about 1 to about 6% w/w peracid.

5. A solution according to any one of claims 1, 2 or 3, wherein the peracid comprises peracetic acid.

6. A solution according to claim 5, wherein the solution comprises from 1 to 6% w/w peracetic acid.

7. A solution according to any one of claims 1, 2, 3 or 6, wherein the solution contains up to 0.5% w/w of a quaternary ammonium cationic surfactant.

8. In a process for disinfection of a substrate, in which the substrate is contacted with a disinfectant solution, the improvement wherein the disinfectant solution comprises an aqueous solution comprising an amount effective for disinfection of an aliphatic peracid containing up to 9 carbon atoms and an ethoxylated and propoxylated alcohol nonionic surfactant according to the general formula:

$$R\text{-}(OCH_2CH_2)_n\text{-}(OCH_2CHCH_3)_p\text{-}OH$$

wherein R represents an alkyl group of at least 6 carbon atoms and n and p each represent an integer.

9. A process according to claim 8, wherein the nonionic surfactant and peracid are present in a weight ratio within the range of from 10:1 to 1:5.

10. A process according to claim 7, wherein the nonionic surfactant and peracid are present in a weight ratio within the range of from 4:1 to 1:1.

11. A process according to claim 8, wherein the aliphatic peracid comprises from 1 to 6% w/w peracetic acid.

12. A process according to any one of claim 8, 9, 10 or 11, further comprising diluting the solution.

13. A process according to any one of claim 8, 9, 10 or 11, wherein disinfection is effected without diluting the solution.

14. A process according to claim 8, 9, 10 or 11, wherein the process is carried out at a pH of at least 6.

15. A process according to claim 8, wherein the solution contains up to 0.5% w/w of a quaternary ammonium cationic surfactant.

16. A process according to claim 8, wherein the process is carried out at a pH of from pH 6 to 8.

17. A process for preparing an aqueous storage stable disinfectant solution which comprises mixing an aqueous solution comprising an aliphatic peracid containing up to 9 carbon atoms with a solution comprising an ethoxylated and propoxylated alcohol nonionic surfactant according to the general formula:

$$R\text{-}(OCH_2CH_2)_n\text{-}(OCH_2CHCH_3)_p\text{-}OH$$

wherein R represents an alkyl group of at least 6 carbon atoms and n and p each represent an integer.

* * * * *